(12) United States Patent
Kugler et al.

(10) Patent No.: US 6,245,784 B1
(45) Date of Patent: Jun. 12, 2001

(54) ANTIFOULING COMPOSITIONS CONTAINING THIACLOPRID

(75) Inventors: Martin Kugler, Leichlingen; Franz Kunisch, Odenthal; Oliver Kretschik, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/538,393

(22) Filed: Mar. 29, 2000

(30) Foreign Application Priority Data

Apr. 7, 1999 (DE) ............................................... 199 15 476
May 4, 1999 (DE) ............................................... 199 22 401

(51) Int. Cl.$^7$ .......................... A01N 43/40; A01N 43/36
(52) U.S. Cl. ...................... 514/342; 504/156; 504/130; 504/244; 504/252
(58) Field of Search ...................... 504/130, 156, 504/244, 252; 514/342

(56) References Cited

U.S. PATENT DOCUMENTS

| | | | |
|---|---|---|---|
| 4,849,432 | * | 7/1989 | Shiokawa et al. .................. 514/341 |
| 5,504,081 | | 4/1996 | Löhr et al. ............................ 514/225 |
| 5,990,043 | | 11/1999 | Kugler et al. ........................ 504/116 |

FOREIGN PATENT DOCUMENTS

97/15192    5/1997    (WO) .

OTHER PUBLICATIONS

STN–International, Accession No. 1998–88049, XP002142576, Zusammenfassung, & Crop Prot., Bd. 17, Nr. 5, 1998, pp. 401–404, I. G. Borlongan et al "Molluscicidal Activity of Tobacco Dust Against Brackishwater Pond Snails (Cerithidae Cingulata Gmelin".
STN–International, Accession No. 1992–87825 Cropu XP002142577, Zusammenfassung, & Biosci. Biotechnol. Biochem., Bd. 56, Nr. 8, 1992, pp. 1208–1211, R. Takasawa et al, "An Efficient Laboratory Matching and Screening Method for Antifouling Substances using the Blue Mussel Mytilus Edulis, and an Antimicrobial Assay".

* cited by examiner

Primary Examiner—Allen J. Robinson
Assistant Examiner—Alton Pryor
(74) Attorney, Agent, or Firm—Joseph C. Gil; Richard E. L. Henderson; Diderico van Eyl

(57) ABSTRACT

Described is a process and, respectively, a composition for protecting articles which come into contact with salt water or brackish water. The compositions comprise as central component thiacloprid.

1 Claim, No Drawings

ANTIFOULING COMPOSITIONS CONTAINING THIACLOPRID

The present invention relates to a process and composition for protecting articles against infestation, especially ships' hulls, screens, nets, constructions, quays and signalling equipment which come into contact with salt water or brackish water.

Infestation by sessile Oligochaetes, such as Serpulidae, and by bivalves and species of the group Lepadomorpha (goose barnacles), such as various Lepas and Scalpellum species, or by species of the group Balanomorpha (acorn barnacles), such as Balanus or Pollicipes species, increases the frictional resistance of ships and leads as a result, through increased energy consumption and, furthermore, through frequent spells in dry dock, to a marked increase in the operating costs.

In addition to infestation by algae, for example Ectocarpus species and Ceramium species, particular importance attaches to infestation by sessile Entomostraca groups, which are comprised under the name Cirripedia (cirriped crustaceans).

It is already known that N-[3-(6-chloropyridin-3-ylmethyl)thiazolidin-2-ylidene]cyanamide (thiacloprid) of the formula

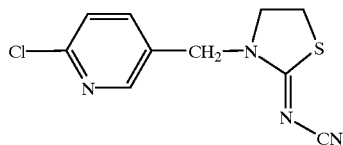

possesses insecticidal properties (EP 235 725).

It has now surprisingly been found that thiacloprid, alone or in combination with other active substances, has an outstanding antifouling (antiinfestation) effect.

The use of thiacloprid alone or in combination with other active substances makes it possible to dispense with the use of heavy metals such as, for example, in bis(trialkyltin) sulfides, tri-n-butyltin laurate, tri-n-butyltin chloride, copper (I) oxide, triethyltin chloride, tri-n-butyl-(2-phenyl-4-chlorophenoxy)-tin, tributyltin oxide, molybdenum disulfide, antimony oxide, polymeric butyl titanate, phenyl (bispyridine)-bismuth chloride, tri-n-butyltin fluoride, manganese ethylenebisdithiocarbamate, zinc dimethyldithiocarbamate, zinc ethylenebisdithiocarbamate, zinc salt of 2-pyridinethiol 1-oxide, bisdimethyldithiocarbamoylzinc ethylenebisdithiocarbamate, zinc oxide, copper (I) ethylenebisdithiocarbamate, copper thiocyanate, copper naphthenate and tributyltin halides or to reduce significantly the concentration of these compounds.

The specification therefore relates to antifouling compositions comprising either thiacloprid alone or thiacloprid in combination with other active substances, preferably algicides, fungicides, herbicides, molluscicides and/or other active antifouling substances.

The invention also relates to a process for protecting articles against infestation, which consists in applying the antifouling compositions of the invention to the articles or adding the antifouling composition to the articles.

The invention also relates to the use of the antifouling compositions of the invention for protecting articles against infestation, especially against infestation by sessile Entomostraca and sessile Oligochaetes.

Suitable co-components for the antifouling compositions of the invention are preferably:

Algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic cyclohexylamide S,S-dioxide, dichlofluanid, fluorfolpet, 3-iodo-2-propinylbutyl carbamate, tolylfluanid and azoles such as azaconazole, cyproconazole, epoxiconazole, hexaconazole, metconazole, propiconazole and tebuconazole;

molluscicides such as fentin acetate, metaldehyde, methiocarb, niclosamide, thiodicarb and trimethacarb;

or conventional active antifouling substances such as 4,5-dichloro-2-octyl-4-isothiazolin-3-one, diiodomethylparatryl sulfone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetramethylthiuram disulfide and 2,4,6-trichlorophenylmaleimide.

The antifouling compositions used contain the active substance of the invention in a concentration of from 0.001 to 50% by weight, in particular from 0.01 to 20% by weight.

The antifouling compositions of the invention usually further comprise—though without being restricted thereto—the customary constituents as described, for example, in Ungerer, Chem. Ind. 1985, 37, 730–732 and Williams, Antifouling Marine Coatings, Noyes, Park Ridge, 1973.

In addition to the algicidal, fingicidal, molluscicidal and—in accordance with the invention—insecticidal active substances, antifouling coating compositions include, in particular, binders.

Examples of recognized binders are polyvinyl chloride in a solvent system, chlorinated rubber in a solvent system, acrylic resins in a solvent system, especially in an aqueous system, vinyl chloride—vinyl acetate copolymer systems in the form of aqueous dispersions or in the form or organic solvent systems, butadiene-styrene-acrylonitrile rubbers, drying oils, such as linseed oil, resin esters or modified hard resins in combination with tar or bitumins, asphalt, and also epoxy compounds, small amounts of chlorinated rubber, chlorinated polypropylene, and vinyl resins.

Coating compositions may also include inorganic pigments, organic pigments or dyes, which are preferably insoluble in salt water. Coating compositions may also include materials such as rosin, in order to allow controlled release of the active substances. The coatings may further comprise plasticizers, modifying agents which influence the rheological properties, and other conventional constituents. Thiacloprid or the thiacloprid combinations of the invention can also be incorporated in self-polishing antifouling systems.

What is claimed is:

1. A method for protecting an article from infestation by sessile Entomostraca and/or sessile Oligochaetes comprising applying to or adding to the article an antifouling composition comprising thiacloprid or thiacloprid in combination with other active antifouling substances.

* * * * *